United States Patent [19]
Venkatesh et al.

[11] Patent Number: 5,633,712
[45] Date of Patent: May 27, 1997

[54] METHOD AND APPARATUS FOR DETERMINING THE THICKNESS AND INDEX OF REFRACTION OF A FILM USING LOW COHERENCE REFLECTOMETRY AND A REFERENCE SURFACES

[75] Inventors: Shalini Venkatesh, Santa Clara; Wayne V. Sorin, Mountain View; Brian L. Heffner, Los Altos, all of Calif.

[73] Assignee: Hewlett-Packard Company, Palo Alto, Calif.

[21] Appl. No.: 520,198

[22] Filed: Aug. 28, 1995

[51] Int. Cl.$^6$ ...................................... G01B 9/02
[52] U.S. Cl. ............................... 356/345; 356/357
[58] Field of Search .............................. 356/73.1, 345, 356/357, 359, 360

[56] References Cited

U.S. PATENT DOCUMENTS

| | | | |
|---|---|---|---|
| 5,341,205 | 8/1994 | McLandrich et al. | 356/357 |
| 5,361,130 | 11/1994 | Kersey et al. | 356/345 |
| 5,473,432 | 12/1995 | Sorin | 356/357 |

*Primary Examiner*—Frank G. Font
*Assistant Examiner*—Robert Kim

[57] ABSTRACT

An apparatus and method for measuring the thickness of a film having top and bottom surfaces. The apparatus includes low coherence light source that generates a probe light signal. The film is positioned between first and second reference reflectors, the first reference reflector being partially reflecting. The probe light signal is applied to the film after passing through the first reference reflector. Part of the portion of the probe light signal leaving the film is reflected back toward the first reference reflector by the second reference reflector. The light exiting through the first reference reflector is collected to form the input to a receiver that determines the time delay between light reflected from the top and bottom surfaces of the film as well as the change in optical path length between said first and second reflectors resulting from the introduction of said film between said first and second reflectors. In the preferred embodiment of the present invention, the receiver is constructed from an optical autocorrelator or an optical spectrum analyzer that includes circuitry for providing the Fourier transform of the frequency domain spectrum measured from the combined light signal. Embodiments in which only one of the reference reflectors is utilized provide a means for simplifying the output spectrum from the receiver when multi-layer films are utilized.

10 Claims, 5 Drawing Sheets

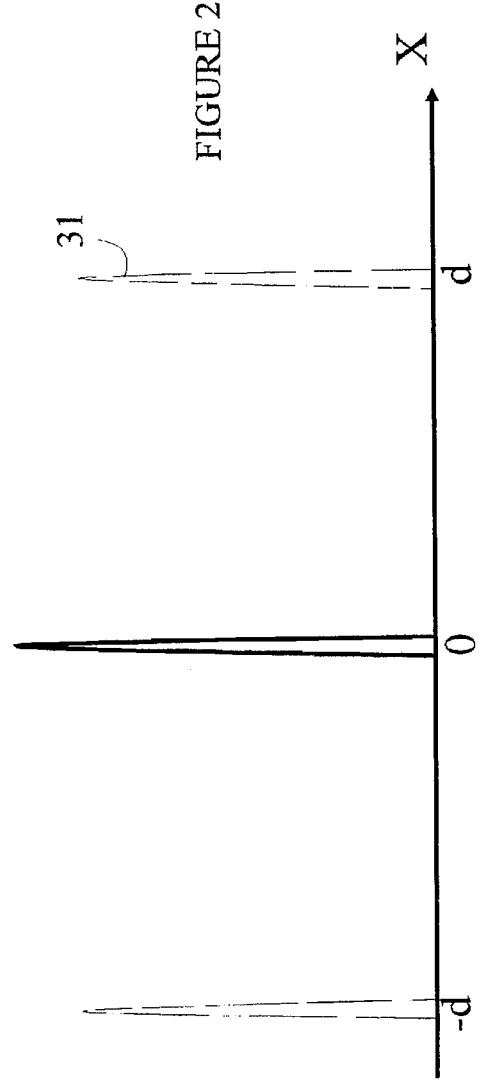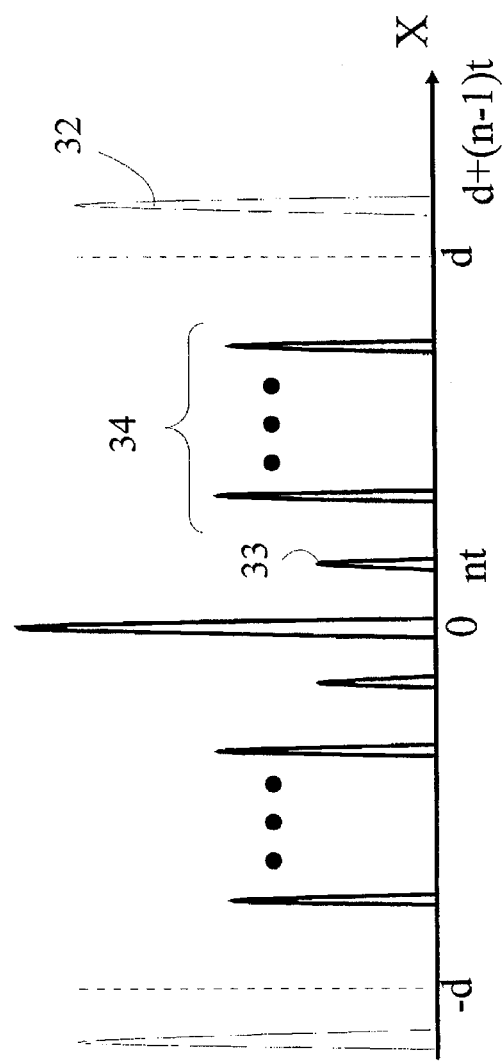

METHOD AND APPARATUS FOR DETERMINING THE THICKNESS AND INDEX OF REFRACTION OF A FILM USING LOW COHERENCE REFLECTOMETRY AND A REFERENCE SURFACES

FIELD OF THE INVENTION

The present invention relates to optical reflectometry, and more particularly, to an apparatus for measuring the thickness and group index of a film, web or sheet.

BACKGROUND OF THE INVENTION

In many industrial processes, control of film thickness is of critical importance. For example, the manufacture of photographic film requires the generation of a uniform layer of emulsion on a backing. From the point of view of process control, it is advantageous to be able to measure the film thickness during the film generation process rather than measuring the film in a laboratory after the film has been manufactured. If samples are measured off-line, correction of any machinery malfunction cannot be performed until after a considerable volume of defective material has been processed. This leads to waste. For the purposes of the present discussion, the term "film" includes sheets and webs.

Prior art methods for measuring film thickness may be divided into contact and non-contact methods. In one contact method, a micrometer that comes in physical contact with both sides of the film is employed. These methods have the disadvantage of physically deforming the film during the measurement leading to inaccurate measurements and possible damage to the film from pitting or scratching. In addition, the methods are difficult to apply for the on-line measurement of fast moving film webs.

Non-contact methods based on the attenuation of a beam of subatomic particles or radiation such as beta particles or gamma rays are also known to the prior art. For example, the attenuation of a beam of electrons by the film is used to determine the film thickness in one prior art method of this type. This methodology has four disadvantages. First, the system must be calibrated for each type of film, since the attenuation depends on the chemical composition and density of the film. Second, the system typically relies on a radioactive source to generate the particle beam. It is generally desirable to limit the use of radioactive material for cost, safety, and psychological reasons. Third, access is normally required to both sides of the film so that the source can be placed on one side and the detector on the other. Finally, this method cannot determine the individual thicknesses in a multi-layer film.

Methods for measuring the thickness of films using an optical autocorrelator are also known to prior art. For the purposes of this discussion, an optical autocorrelator is defined to be an interferometer having a variable differential time delay. One embodiment of an optical autocorrelator is described, for example, in chapter 5 of *Statistical Optics*, by Joseph W. Goodman (John Wiley & Sons, 1985, pp. 157–170). Those skilled in the art are aware of the principles of operation of an optical autocorrelator, but certain principles will be clarified here because of their relevance to this patent. In an autocorrelating interferometer wherein light is split into two different paths and then recombined and directed to a photodiode, the detected light intensity is measured as a function of a parameter. This parameter can be the differential optical path length $\Delta L$ of the interferometer or it can be the differential time delay $\Delta t$ of the interferometer. These parameters are related by $\Delta L = nc\Delta t$, where c is the speed of light in vacuum and n is the group index of the medium (usually air) of the differential optical path. The detected light intensity expressed as a function of the differential time delay is called the coherence function of the input light. Hence, a receiver which determines the time delay between light reflected from different surfaces of a film performs the same function as a receiver which determines the path delay between light reflected from different surfaces of a film. Determining the spacing between peaks in the coherence function of the reflected light is yet another way to describe the same function. For the purposes of the present discussion, the term differential time delay shall include differential path delay.

A Michelson interferometer is an example of such an autocorrelator. An example of an apparatus for measuring film thickness which utilizes a Michelson interferometer is taught in U.S. Pat. No. 3,319,515 to Flournoy. In this system, the film is illuminated with a collimated light beam at an angle with respect to the surface of the film. The front and back surfaces of the film generate reflected light signals. The distance between the two reflecting surfaces is then determined by examining the peaks in the autocorrelation spectrum generated in a Michelson interferometer that receives the reflected light as its input. Unfortunately, this method can determine only the product of the group index and the film thickness. If a variation is detected in this quantity, additional measurements must be made to determine if the film composition has changed or the thickness has changed. The group index is defined to be the ratio of the propagation velocity of a light pulse in the medium relative to the velocity of propagation of the pulse in a vacuum.

If the film consists of a number of layers having different thicknesses or indicies of refraction, the above method cannot always provide an unambiguous answer with respect to the product of the thickness and index of refraction for each layer. The output of the autocorrelating interferometer consists of a number of peaks whose locations depend n the difference in optical path length for each possible pair of reflecting boundaries. As the number of boundaries increases, the number of peaks increases rapidly. For example, a three layer film will generate an output having 13 peaks corresponding to the various "single pass" reflections in the system described above. There will be additional peaks corresponding to light that is reflected more than once in the film.

Broadly, it is the object of the present invention to provide an improved apparatus and method for measuring the thickness and index of refraction of a thin film.

It is a further object of the present invention to a system that does not require contact between the film and the measuring device.

It is a still further object of the present invention to provide a system that is independent of length variations in the fiber leads and, in the case of a single layer film, can also accommodate flutter in the film.

It is yet another object of the present invention to provide a system that can determine both the group index and the film thickness independently.

It is a still further object of the present invention to provide a system that can determine the thicknesses of the various layers in a multi-layer film.

These and other objects of the present invention will become apparent to those skilled in the art from the following detailed description of the invention and the accompanying drawings.

SUMMARY OF THE INVENTION

The present invention comprises an apparatus and method for measuring the thickness of a film having top and bottom surfaces. The apparatus includes a low coherence light source that generates a probe light signal. The film is positioned between first and second reference reflectors, the first reference reflector being partially reflecting. The probe light signal is applied to the film after passing through the first reference reflector. The portion of the probe light signal leaving the film is reflected back toward the first reference reflector by the second reference reflector. The light exiting through the first reference reflector is collected to form the input to a receiver that determines the time delay between light reflected from the top and bottom surfaces of the film as well as the change in optical path length between said first and second reflectors resulting from the introduction of said film between said first and second reflectors. In the preferred embodiment of the present invention, the receiver is constructed from an optical autocorrelator or an optical spectrum analyzer that includes circuitry for providing the Fourier transform of the frequency domain spectrum measured from the combined light signal. Embodiments in which only one of the reference reflectors is utilized provide a means for simplifying the output spectrum from the receiver when multi-layer films are utilized.

BRIEF DESCRIPTION OF THE DRAWINGS

FIG. 2 illustrates the output generated by an autocorrelation receiver when no film is present between the reference reflectors.

FIG. 3 illustrates the output generated by an autocorrelation receiver when the film to be measured is introduced between the reference reflectors.

DETAILED DESCRIPTION OF THE INVENTION

Figure 1:
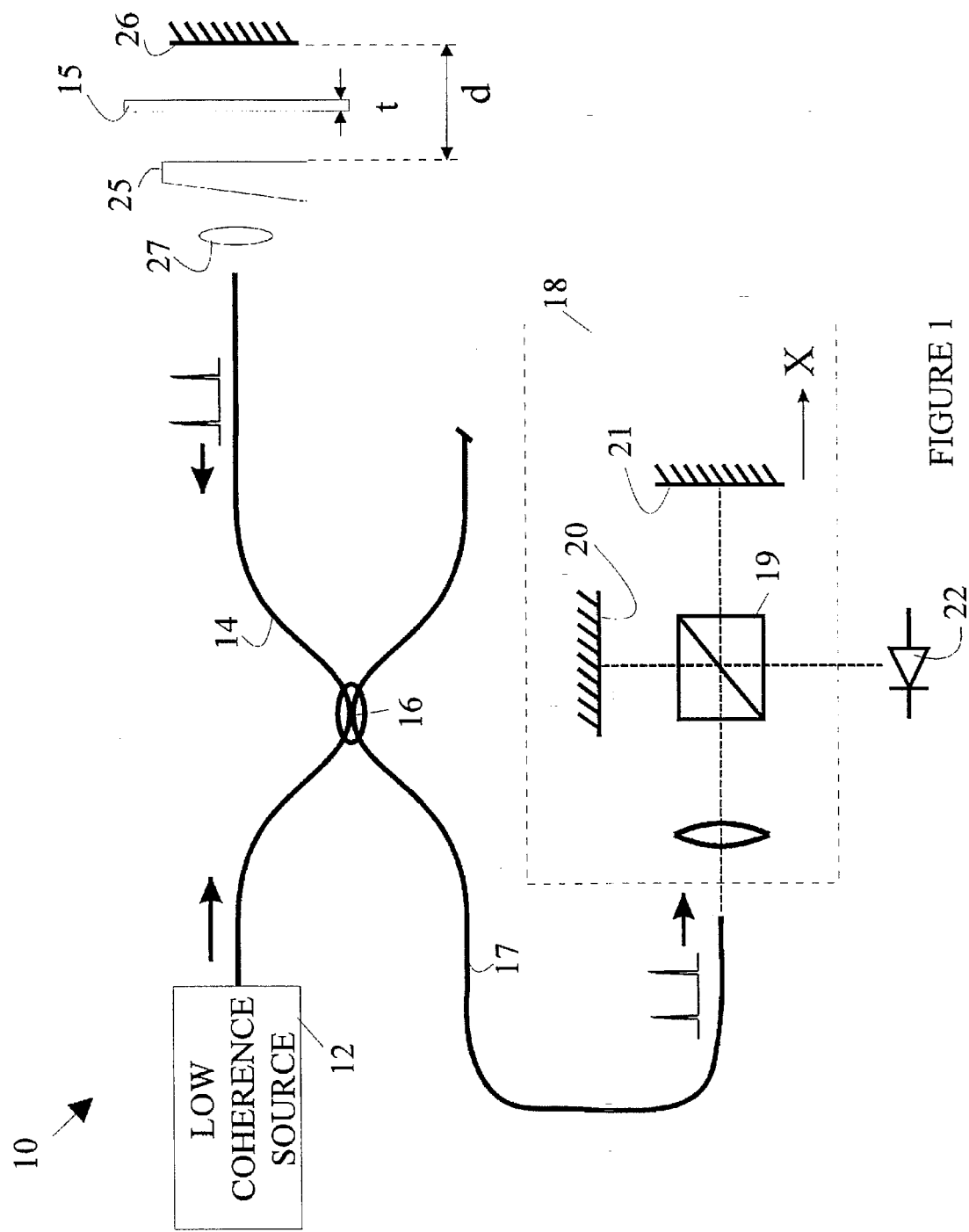
FIG. 1 is a schematic drawing of the preferred embodiment of a thickness monitoring apparatus according to the present invention.

The method by which the present invention attains its advantages over the prior art may be more easily understood with reference to FIG. 1 which is a schematic drawing of the preferred embodiment of a thickness monitoring apparatus according to the present invention. Apparatus 10 utilizes a low coherence light source 12 to generate a light signal that is applied to the film 15 to be measured after passing through reference plate 25 whose function will be discussed in more detail below. A second reference reflector 26 is located behind film 15. Reference reflector 26 can also be a partially reflecting surface. Light reflected back into fiber 14 is collected by lens 27 and routed to a receiver 18 with the aid of a coupler 16 and fiber 17. Receiver 18 is preferably an autocorrelator; however, as will be explained in more detail below, other forms of receivers may be utilized.

The coherence length of light source 12 must be small compared to the thickness of the film being measured. Such light sources are common in the optical reflectometry arts, and hence, will not be discussed in detail here. For the purposes of the present discussion, it is sufficient to note that an edge emitting light emitting diode may be utilized for light source 12.

An exemplary autocorrelator 18 constructed from a Michelson interferometer is shown at 18. The light incident on Michelson interferometer is split into two beams that traverse different paths by beam splitter 19. The first path is determined by the position of fixed mirror 20 and the second by moveable mirror 21. After traversing the different paths, the light is recombined by splitter 19 and directed to a photodiode 22 which measures the intensity of the light which varies with the position of mirror 21 due to the interference of the light.

Whenever the difference in the reference arms of the interferometer is equal to the difference in optical path length between two different surfaces that have reflected the light, a peak in intensity will be generated at photodiode 22. There will always be a large peak at x=0 corresponding to the case in which each reflection overlaps with itself.

Refer now to FIGS. 2 and 3 which illustrate, respectively, the output of receiver 18 before and after the film is placed in the gap between plate 25 and reflector 26. In the absence of the film, the output of receiver 18 will include a peak at x=d, the spacing between the reference reflectors. When the film is introduced, this peak will move to x=d+(n−1)t as shown in FIG. 3 at 32. In principle, there will also be peaks corresponding to the surface of reflector 25 nearest to lens 27. Since reflections from this additional surface do not provide any additional useful information, these reflections can be supressed by angling the surface or coating the surface with an antireflection coating.

The insertion of film into the gap will also give rise to a number of other peaks resulting from reflections from the various new combinations of surfaces involving one surface of the film and one of the reference surfaces. Exemplary peaks of this type are shown at 34 in FIG. 3. Finally, there will be one peak corresponding to the reflections from the two surfaces of the film. This peak will be at x=nt as shown at 33 in FIG. 3. It should be noted that a second set of peaks symmetrically located about x=0 will also be present in the output of receiver 18.

If a single uniform film is present in the gap, the shift in the peak 31 and the location of peak 33 provides sufficient information to determine both n and t. If more than one layer is present, the additional reflections may be used to simplify the interpretation of the peak pattern thereby allowing information on the thickness of each layer to be obtained.

Figure 4:
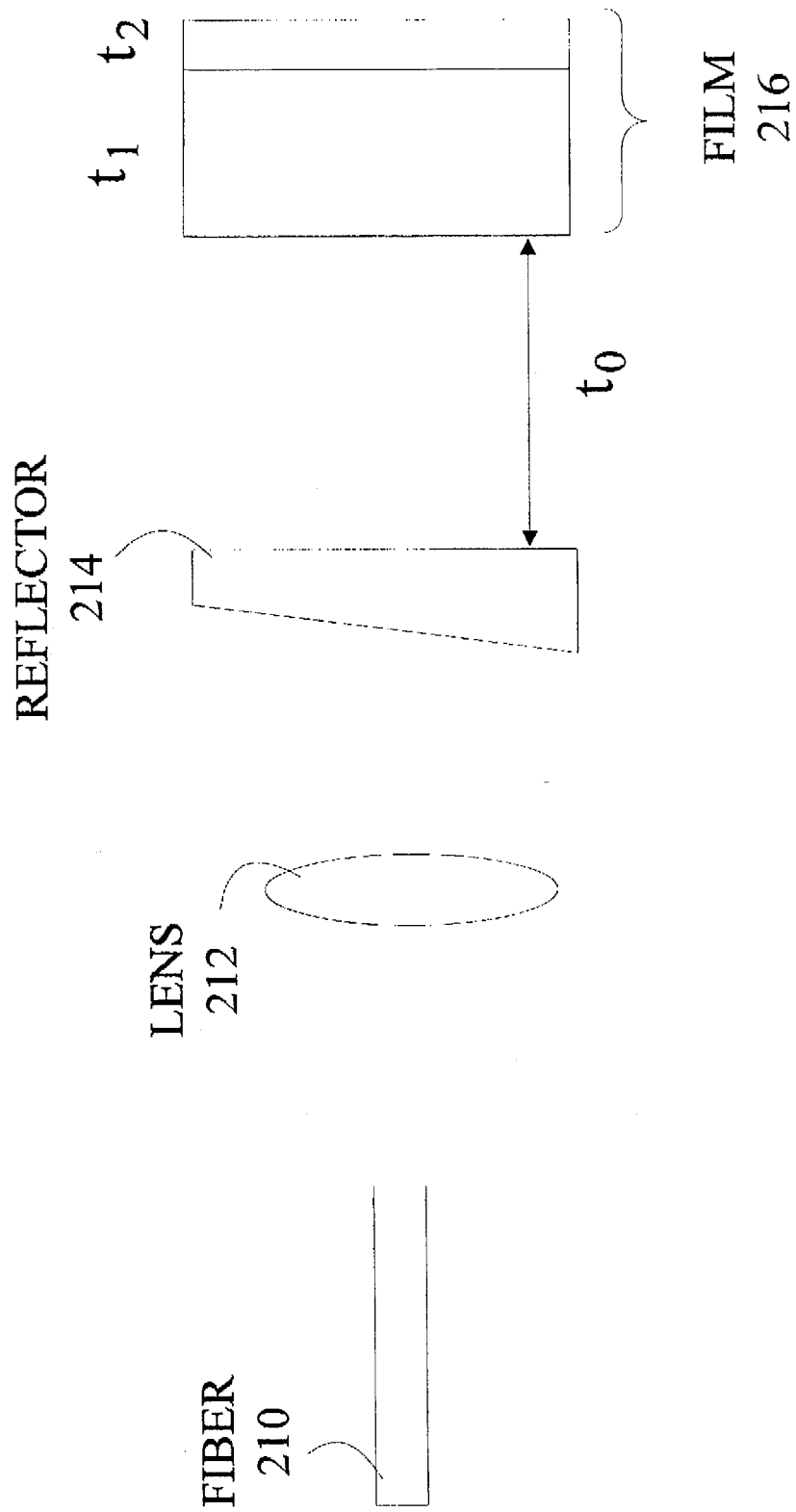
FIG. 4 illustrates an arrangement in which one reflector is used to simplify the interpretation of the output of the autocorrelator when a two layer film is measured.
Figure 5:
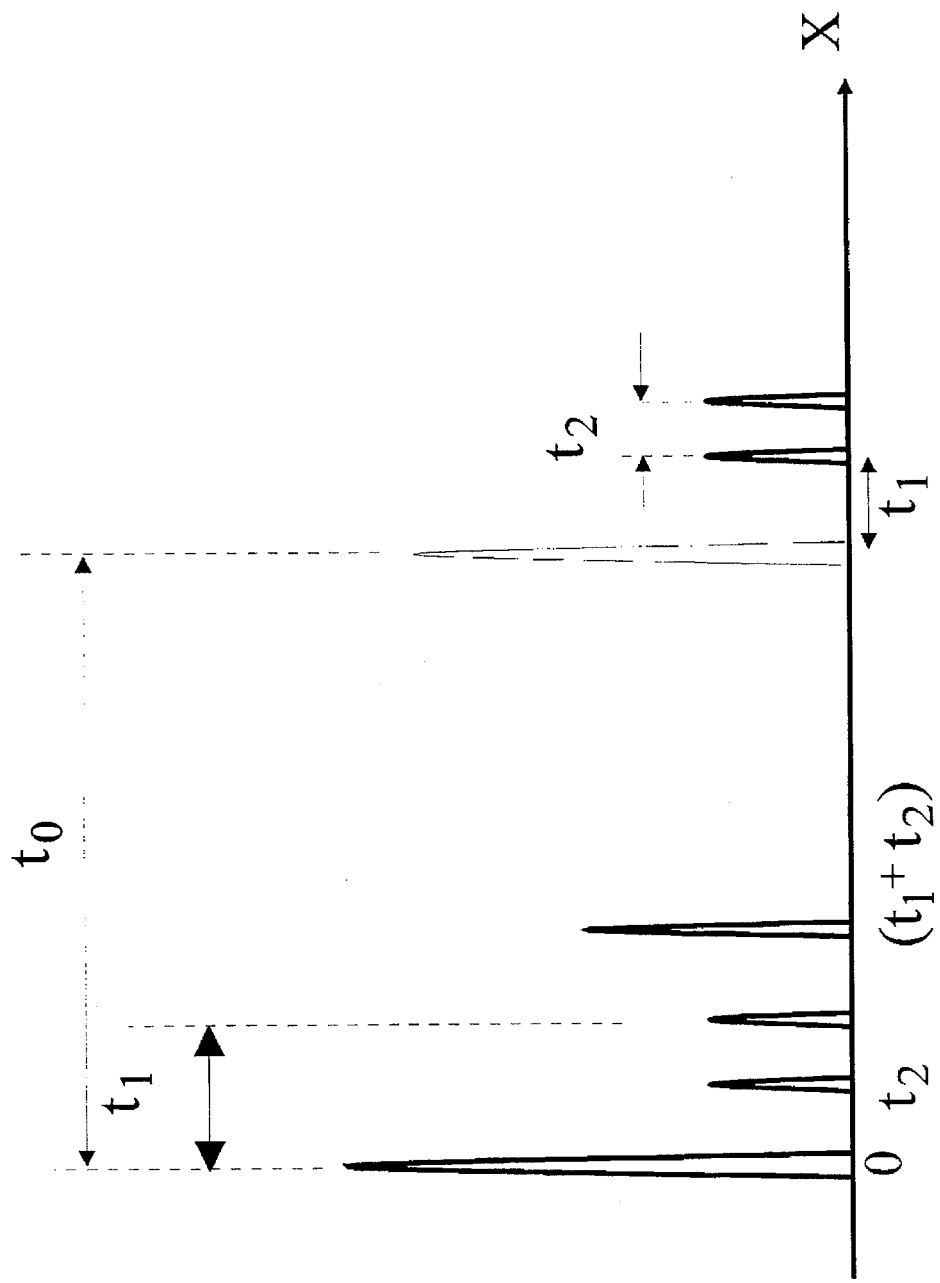
FIG. 5 illustrates the output generated by an autocorrelator receiver when the arrangement shown in FIG. 4 is utilized.

Consider the case in which the film consists of two layers and in which the reference reflector in front of the film has a reflectivity that is substantially larger than that of the various film boundaries. Such an arrangement is shown in FIG. 4. Light delivered by fiber 210 is colliminated by a lens 212 and then passes through a partially reflecting plate 214 and impinges on a two layer film 216. Denote the distance from the reference reflector to the surface of the first layer by $t_0$. Similarly, denote the thicknesses of the first and second layers by $t_1$ and $t_2$, respectively. There are three possible combinations of reflections between the reference surface and the boundaries of the film. These reflections will correspond to x values of $t_0$, $(t_0+n_1t_1)$, and $(t_0+n_1t_1+n_2t_2)$, where $n_1$ and $n_2$ are the respective indices of refraction of the first and second layers. The peaks corresponding to these reflections are shown in FIG. 5. To simplify the drawing, the group index values have been omitted, i.e., $n_1t_1$ is shown as $t_1$. It should be noted that $t_0$ may be adjusted to provide a spacing for these peaks that is clear of any other peaks in the output of the receiver. It should also be noted that the order of the peaks in the spectrum is the same as the spatial ordering of the layers. Hence, the reference reflector also provides a means for simplifying the interpretation of the output of the receiver. The simplification of the autocorrelator output from receiver 18 requires only one reference reflector. Either of the reflectors 25 and 26 shown in FIG. 1 will function for this purpose.

In some applications, the measurement of the thickness at a number of different locations on the sheet is desired to test for uniformity across the sheet. The present invention can provide such multi-point measurements by inserting additional 3 dB couplers in fiber 14 or using the additonal fiber leaving coupler 16 as shown in FIG. 1 so as to split the signal into additional fibers to be used in constructing additional probes. If the dimensions of each probe are chosen to be sufficiently different from the other probes, and the distances from the film to the reference surfaces are likewise chosen to be different, the various probe measurements can be multiplexed onto the same autocorrelator. The additional peaks introduced by the additional probe pairs will be distinct from each other if sufficient differences exist.

Although the above described embodiments of the present invention have utilized a Michelson interferometer as the autocorrelator, other forms of autocorrelator may be utilized. For example, an optical spectrum analyzer which measures the optical power as a function of wavelength or optical frequency can be utilized. The Fourier transform of the frequency domain spectrum provides an output which is identical to that of an autocorrelator.

Figure 6:
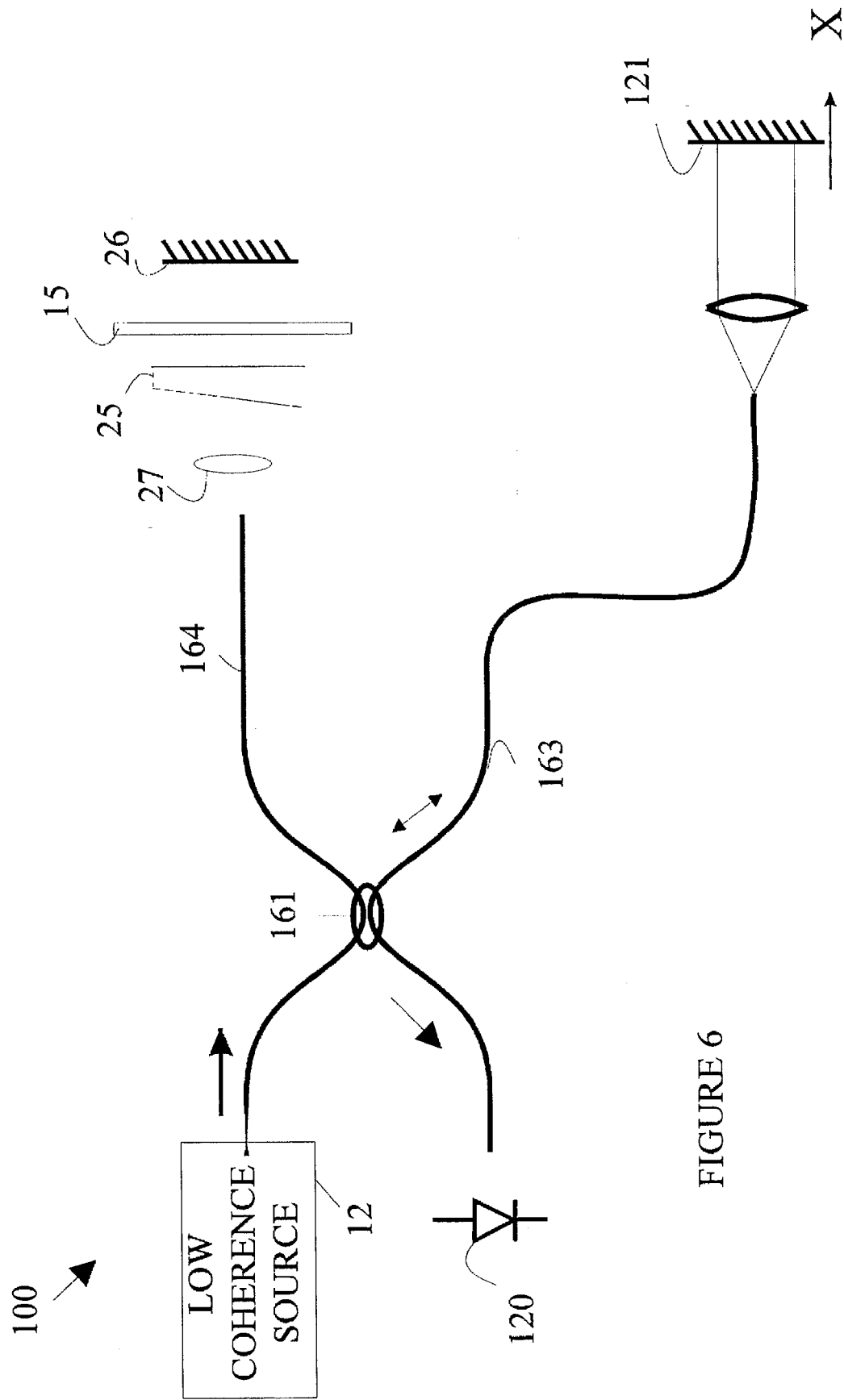
FIG. 6 is a schematic drawing of an embodiment of the present invention utilizing an optical reflectometer for the receiver.

While the above described embodiments of the present invention have utilized an autocorrelator for the receiver other types of reflectometer receivers may also be utilized. Such an alternate arrangement is shown at 100 in FIG. 6. The light from a low coherence source 12 is split into two signals by a coupler 161. The signal on fiber 164 is applied to the film to be measured as described above. The light reflected back into fiber 164 is combined with the second light signal generated by coupler 161 at coupler 161 after the second light signal has traversed a variable reference path comprising moving mirror 121. The signals combined at coupler 161 will undergo constructive interference when the delay in the reference path matches the transit time for the signals on the probe arm of the reflector. The intensity of the light leaving coupler 161 is measured by a photodetector 121. This type of receiver may be purchased commercially (Hewlett Packard HP8504 Precision Reflectomer). From the output of the photodiode as a function of the mirror position X, the film thickness and group index of refraction may be determined as discussed above.

Any type of reflectometer having sufficient spatial resolution to distinguish the film reflections can be used in this configuration. This configuration, however, is not preferred because the results are sensitive to variations in the lengths of the various fibers. Such variations may occur due to temperature fluctuations or mechanical stress. In contrast, the results obtained with an autocorrelating receiver are independent of such fluctuations.

While the present invention has been described in terms of a film having "top" and "bottom" surfaces, these terms are merely convienent labels for the two surfaces of the film. Hence, these terms are not to be taken as limiting the scope of the present invention.

Various modifications to the present invention will become apparent to those skilled in the art from the foregoing description and accompanying drawings. Accordingly, the present invention is to be limited solely by the scope of the following claims.

What is claimed is:

1. An apparatus for measuring the thickness and group index of a transparent film having top and bottom surfaces, said apparatus comprising:

means for generating a probe light signal from a low coherence light source and applying said probe light signal to said film;

a first reflector, said first reflector being partially transparent;

a second reflector, said film being positioned between said first and second reflectors, said probe light signal being applied to said film after passing through said first reflector, said second reflector reflecting a portion of said probe light signal leaving said film back toward said first reflector;

means for collecting light reflected back toward said first reflector; and a receiver for receiving said collected light signal and for determining the time delay between light reflected from said top and bottom surfaces of said film from said collected light and for determining the change in optical path between said first and second reflectors when said film is placed between said first and second reflectors, said thickness and group index being determined from said time delay and said change in optical path.

2. The apparatus of claim 1 wherein said receiver comprises an optical autocorrelator.

3. The apparatus of claim 1 wherein said receiver comprises an optical reflectometer.

4. The apparatus of claim 1 wherein said receiver comprises an optical spectrum analyzer.

5. An apparatus for measuring the thicknesses of the layers of a multilayer transparent film having top and bottom surfaces, said apparatus comprising:

means for generating a probe light signal from a low coherence light source and applying said probe light signal to said film;

a partial reflector positioned on one side of said film such that said reflector reflects a portion of said probe light signal;

means for collecting light reflected by said reflector and said film; and a receiver for receiving said collected light signal and for determining the time delay between light reflected from said top and bottom surfaces and one or more internal layer interfaces of said film and said reflector.

6. A method for measuring the thickness and group index of refraction of a transparent film having top and bottom surfaces, said method comprising the steps of:

generating a probe light signal from a low coherence light source and applying said probe light signal to said film;

providing a first reflector, said first reflector being partially transparent;

providing a second reflector, said film being positioned between said first and second reflectors, said probe light signal being applied to said film after passing through said first reflector, said second reflector reflecting the portion of said probe light signal leaving said film back toward said first reflector;

collecting light reflected back toward said first reflector; and determining the time delay between light reflected from said top and bottom surfaces of said film from said collected light and for determining the change in optical path between said first and second reflectors when said film is placed between said first and second reflectors in a receiver, said thickness and group index being determined from said time delay and said change in optical path.

7. The method of claim 6 wherein said receiver comprises an optical autocorrelator.

8. The method of claim 6 wherein said receiver comprises an optical reflectometer.

9. The method of claim 6 wherein said receiver comprises an optical spectrum analyzer.

10. A method for measuring the thicknesses of the layers of a multilayer transparent film having top and bottom surfaces and one or more internal layer interfaces, said method comprising the steps of:

generating a probe light signal from a low coherence light source and applying said probe light signal to said film;

providing a reflector to reflect a portion of said probe light signal;

collecting light reflected by said film and said reflector; and determining the time delay between light reflected from said top and bottom surfaces and said internal layer interfaces of said film and said reflector from said collected light.

* * * * *

UNITED STATES PATENT AND TRADEMARK OFFICE
CERTIFICATE OF CORRECTION

PATENT NO. : 5,633,712
DATED : May 27, 1997
INVENTOR(S) : Venkatesh, et al.

It is certified that error appears in the above-indentified patent and that said Letters Patent is hereby corrected as shown below:

Column 1, line 67, "$\Delta L = nc\Delta t$," should read

-- $\Delta L = c\Delta t/n$, --;

Column 2, line 30, "the medium" should read
-- a vacuum --;

Title page, item [54] and Col. 1,
Title, "Method and Apparatus for Determining the Thickness and Index of Refraction of a Film Using Low Coherence Reflectometry and a Reference Surfaces", should read -- Method and Apparatus for Determining the Thickness and Index of Refraction of a Film Using Low Coherence Reflectometry and a Reference Surface --.

Signed and Sealed this

Twenty-eighth Day of July, 1998

Attest:

BRUCE LEHMAN

*Attesting Officer*   *Commissioner of Patents and Trademarks*